(12) United States Patent
Ljungblad

(10) Patent No.: US 10,144,063 B2
(45) Date of Patent: Dec. 4, 2018

(54) METHOD AND APPARATUS FOR DETECTING DEFECTS IN FREEFORM FABRICATION

(71) Applicant: ARCAM AB, Moelndal (SE)

(72) Inventor: Ulric Ljungblad, Moelndal (SE)

(73) Assignee: ARCAM AB, Moelndal (SE)

( * ) Notice: Subject to any disclaimer, the term of this patent is extended or adjusted under 35 U.S.C. 154(b) by 0 days.

(21) Appl. No.: 14/349,283

(22) PCT Filed: Dec. 5, 2012

(86) PCT No.: PCT/EP2012/074535
§ 371 (c)(1),
(2) Date: Apr. 2, 2014

(87) PCT Pub. No.: WO2013/098054
PCT Pub. Date: Jul. 4, 2013

(65) Prior Publication Data
US 2014/0308153 A1    Oct. 16, 2014

Related U.S. Application Data

(60) Provisional application No. 61/580,766, filed on Dec. 28, 2011.

(51) Int. Cl.
| | | |
|---|---|---|
| *B22F 3/105* | (2006.01) | |
| *B29C 67/00* | (2017.01) | |
| *B32B 15/01* | (2006.01) | |
| *C22C 38/00* | (2006.01) | |
| *G01N 21/95* | (2006.01) | |
| *B22F 3/15* | (2006.01) | |
| *C22C 14/00* | (2006.01) | |
| *C22C 19/07* | (2006.01) | |
| *C22C 21/00* | (2006.01) | |

(52) U.S. Cl.
CPC ........ *B22F 3/1055* (2013.01); *B29C 67/0077* (2013.01); *B32B 15/01* (2013.01); *B32B 15/012* (2013.01); *B32B 15/013* (2013.01); *C22C 38/00* (2013.01); *G01N 21/9515* (2013.01); *B22F 3/15* (2013.01); *B22F 2003/1056* (2013.01); *C22C 14/00* (2013.01); *C22C 19/07* (2013.01); *C22C 21/00* (2013.01); *Y02P 10/295* (2015.11)

(58) Field of Classification Search
CPC . B22F 3/1055; B29C 64/0077; B32B 15/012; C22C 38/00; G01N 21/9515
USPC ........................................................ 419/53
See application file for complete search history.

(56) References Cited

U.S. PATENT DOCUMENTS

| | | |
|---|---|---|
| 2,264,968 A | 12/1941 | De Forest |
| 2,323,715 A | 7/1943 | Kuehni |
| 3,634,644 A | 1/1972 | Ogden et al. |
| 3,838,496 A | 10/1974 | Kelly |
| 3,882,477 A | 5/1975 | Mueller |
| 3,906,229 A | 9/1975 | Demeester et al. |
| 3,908,124 A | 9/1975 | Rose |
| 4,314,134 A | 2/1982 | Schumacher et al. |
| 4,348,576 A | 9/1982 | Anderl et al. |
| 4,352,565 A | 10/1982 | Rowe et al. |
| 4,401,719 A | 8/1983 | Kobayashi et al. |
| 4,541,055 A | 9/1985 | Wolfe et al. |
| 4,818,562 A | 4/1989 | Arcella et al. |
| 4,863,538 A | 9/1989 | Deckard |
| 4,888,490 A | 12/1989 | Bass et al. |
| 4,927,992 A | 5/1990 | Whitlow et al. |
| 4,958,431 A | 9/1990 | Clark et al. |
| 4,988,844 A | 1/1991 | Dietrich et al. |
| 5,118,192 A | 6/1992 | Chen et al. |
| 5,135,695 A | 8/1992 | Marcus |
| 5,167,989 A | 12/1992 | Dudek et al. |
| 5,182,170 A | 1/1993 | Marcus et al. |
| 5,204,055 A | 4/1993 | Sachs et al. |
| 5,247,560 A | 9/1993 | Hosokawa et al. |
| 5,393,482 A | 2/1995 | Benda et al. |
| 5,483,036 A | 1/1996 | Giedt et al. |
| 5,511,103 A | 4/1996 | Hasegawa |
| 5,595,670 A | 1/1997 | Mombo Caristan |
| 5,647,931 A | 7/1997 | Retallick et al. |
| 5,753,274 A | 5/1998 | Wilkening et al. |
| 5,837,960 A | 11/1998 | Lewis et al. |
| 5,876,550 A | 3/1999 | Feygin et al. |
| 5,904,890 A | 5/1999 | Lohner et al. |
| 5,932,290 A | 8/1999 | Lombardi et al. |

(Continued)

FOREIGN PATENT DOCUMENTS

| | | |
|---|---|---|
| CA | 2860188 A1 | 6/2006 |
| CN | 101607311 A | 12/2009 |

(Continued)

OTHER PUBLICATIONS

International Searching Authority (ISA), International Search Report and Written Opinion for International Application No. PCT/EP2012/074535, dated Mar. 8, 2013, 12 pages, European Patent Office, The Netherlands.

(Continued)

*Primary Examiner* — Christopher S Kessler
(74) *Attorney, Agent, or Firm* — Alston & Bird LLP

(57) ABSTRACT

A method for detecting defects in three-dimensional articles. Providing a model of said article. Providing a first powder layer on a substrate, directing an energy beam over said substrate causing said first powder layer to fuse in selected locations forming a first cross section of said three-dimensional article, providing a second powder layer on said substrate, directing the energy beam over said substrate causing said second powder layer to fuse in selected locations to form a second cross section of said three-dimensional article. A first and second image of a first and second fusion zone of said first powder layer respectively is captured. Comparing said first and second images with corresponding layers in said model. Detecting a defect in the three-dimensional article if a deviation in said first image with respect to said model is at least partially overlapping a deviation in said second image with respect to said model.

6 Claims, 3 Drawing Sheets

(56) References Cited

U.S. PATENT DOCUMENTS

| | | |
|---|---|---|
| 6,046,426 A | 4/2000 | Jeantette et al. |
| 6,162,378 A | 12/2000 | Bedal et al. |
| 6,419,203 B1 | 7/2002 | Dang |
| 6,537,052 B1 | 3/2003 | Adler |
| 6,554,600 B1 | 4/2003 | Hofmann et al. |
| 6,583,379 B1 | 6/2003 | Meiners et al. |
| 6,676,892 B2 | 1/2004 | Das et al. |
| 6,724,001 B1 | 4/2004 | Pinckney et al. |
| 6,746,506 B2 | 6/2004 | Liu et al. |
| 6,751,516 B1 | 6/2004 | Richardson |
| 6,764,636 B1 | 7/2004 | Allanic et al. |
| 6,811,744 B2 | 11/2004 | Keicher et al. |
| 6,815,636 B2 | 11/2004 | Chung et al. |
| 6,824,714 B1 | 11/2004 | Türck et al. |
| 7,003,864 B2 | 2/2006 | Dirscherl |
| 7,020,539 B1 | 3/2006 | Kovacevic et al. |
| 7,165,498 B2 | 1/2007 | Mackrill et al. |
| 7,204,684 B2 | 4/2007 | Ederer et al. |
| 7,291,002 B2 | 11/2007 | Russell et al. |
| 7,452,500 B2 | 11/2008 | Uckelmann |
| 7,537,722 B2 | 5/2009 | Andersson et al. |
| 7,540,738 B2 | 6/2009 | Larsson et al. |
| 7,635,825 B2 | 12/2009 | Larsson |
| 7,686,605 B2 | 3/2010 | Perret et al. |
| 7,696,501 B2 | 4/2010 | Jones |
| 7,713,454 B2 | 5/2010 | Larsson |
| 7,754,135 B2 | 7/2010 | Abe et al. |
| 7,799,253 B2 | 9/2010 | Höchsmann et al. |
| 7,871,551 B2 | 1/2011 | Wallgren et al. |
| 8,021,138 B2 | 9/2011 | Green |
| 8,083,513 B2 | 12/2011 | Montero-Escuder et al. |
| 8,137,739 B2 | 3/2012 | Philippi et al. |
| 8,187,521 B2 | 5/2012 | Larsson et al. |
| 8,308,466 B2 | 11/2012 | Ackelid et al. |
| 8,992,816 B2 | 3/2015 | Jonasson et al. |
| 9,073,265 B2 | 7/2015 | Snis |
| 9,079,248 B2 | 7/2015 | Ackelid |
| 9,126,167 B2 | 9/2015 | Ljungblad |
| 9,310,188 B2 | 4/2016 | Snis |
| 9,505,172 B2 | 11/2016 | Ljungblad |
| 9,550,207 B2 | 1/2017 | Ackelid |
| 2002/0104973 A1 | 8/2002 | Kerekes |
| 2002/0152002 A1 | 10/2002 | Lindemann et al. |
| 2002/0195747 A1 | 12/2002 | Hull et al. |
| 2003/0043360 A1 | 3/2003 | Farnworth |
| 2003/0133822 A1 | 7/2003 | Harryson |
| 2003/0205851 A1 | 11/2003 | Laschutza et al. |
| 2004/0012124 A1 | 1/2004 | Li et al. |
| 2004/0026807 A1 | 2/2004 | Andersson et al. |
| 2004/0084814 A1 | 5/2004 | Boyd et al. |
| 2004/0104499 A1 | 6/2004 | Keller |
| 2004/0148048 A1 | 7/2004 | Farnworth |
| 2004/0173496 A1 | 9/2004 | Srinivasan |
| 2004/0173946 A1 | 9/2004 | Pfeifer et al. |
| 2004/0204765 A1 | 10/2004 | Fenning et al. |
| 2004/0217095 A1 | 11/2004 | Herzog |
| 2005/0173380 A1 | 8/2005 | Carbone |
| 2005/0186538 A1 | 8/2005 | Uckelmann |
| 2005/0282300 A1 | 12/2005 | Yun et al. |
| 2006/0108712 A1 | 5/2006 | Mattes |
| 2006/0138325 A1 | 6/2006 | Choi |
| 2006/0145381 A1 | 7/2006 | Larsson |
| 2006/0147332 A1 | 7/2006 | Jones et al. |
| 2006/0157892 A1 | 7/2006 | Larsson |
| 2006/0180957 A1 | 8/2006 | Hopkinson et al. |
| 2006/0284088 A1 | 12/2006 | Fukunaga et al. |
| 2007/0074659 A1 | 4/2007 | Wahlstrom |
| 2007/0175875 A1 | 8/2007 | Uckelmann et al. |
| 2007/0179655 A1 | 8/2007 | Farnworth |
| 2007/0182289 A1 | 8/2007 | Kigawa et al. |
| 2007/0298182 A1 | 12/2007 | Perret et al. |
| 2008/0236738 A1 | 10/2008 | Lo et al. |
| 2009/0017219 A1 | 1/2009 | Paasche et al. |
| 2009/0152771 A1 | 6/2009 | Philippi et al. |
| 2009/0206056 A1 | 8/2009 | Xu et al. |
| 2010/0007062 A1 | 1/2010 | Larsson et al. |
| 2010/0260410 A1 | 10/2010 | Taminger et al. |
| 2010/0305743 A1 | 12/2010 | Larsson |
| 2010/0310404 A1 | 12/2010 | Ackelid |
| 2010/0316856 A1 | 12/2010 | Currie et al. |
| 2011/0061591 A1 | 3/2011 | Stecker |
| 2011/0114839 A1 | 5/2011 | Stecker et al. |
| 2011/0133367 A1 | 6/2011 | Weidinger et al. |
| 2011/0240607 A1 | 10/2011 | Stecker et al. |
| 2011/0241575 A1 | 10/2011 | Caiafa et al. |
| 2011/0293770 A1 | 12/2011 | Ackelid et al. |
| 2011/0293771 A1 | 12/2011 | Oberhofer et al. |
| 2011/0309554 A1 | 12/2011 | Liska et al. |
| 2011/0316178 A1 | 12/2011 | Uckelmann |
| 2012/0100031 A1 | 4/2012 | Ljungblad |
| 2012/0164322 A1 | 6/2012 | Teulet et al. |
| 2012/0183701 A1 | 7/2012 | Pilz et al. |
| 2012/0193530 A1 | 8/2012 | Parker et al. |
| 2012/0211155 A1 | 8/2012 | Wehning et al. |
| 2012/0223059 A1 | 9/2012 | Ljungblad |
| 2012/0225210 A1 | 9/2012 | Fruth |
| 2012/0237745 A1 | 9/2012 | Dierkes et al. |
| 2012/0266815 A1 | 10/2012 | Brunermer |
| 2013/0055568 A1 | 3/2013 | Dusel et al. |
| 2013/0162134 A1 | 6/2013 | Mattausch et al. |
| 2013/0186514 A1 | 7/2013 | Zhuang et al. |
| 2013/0216959 A1 | 8/2013 | Tanaka et al. |
| 2013/0233846 A1 | 9/2013 | Jakimov et al. |
| 2013/0264750 A1 | 10/2013 | Hofacker et al. |
| 2013/0270750 A1 | 10/2013 | Green |
| 2013/0278920 A1 | 10/2013 | Loewgren |
| 2013/0300286 A1 | 11/2013 | Ljungblad et al. |
| 2013/0343947 A1 | 12/2013 | Satzger et al. |
| 2014/0175708 A1 | 6/2014 | Echigo et al. |
| 2014/0271964 A1 | 9/2014 | Roberts, IV et al. |
| 2014/0301884 A1 | 10/2014 | Hellestam et al. |
| 2014/0314609 A1 | 10/2014 | Ljungblad et al. |
| 2014/0314964 A1 | 10/2014 | Ackelid |
| 2014/0348691 A1 | 11/2014 | Ljungblad et al. |
| 2014/0363327 A1 | 12/2014 | Holcomb |
| 2014/0367367 A1 | 12/2014 | Wood et al. |
| 2015/0004045 A1 | 1/2015 | Ljungblad |
| 2015/0050463 A1 | 2/2015 | Nakano et al. |
| 2015/0071809 A1 | 3/2015 | Nordkvist et al. |
| 2015/0086409 A1 | 3/2015 | Hellestam |
| 2015/0088295 A1 | 3/2015 | Hellestam |
| 2015/0130118 A1 | 5/2015 | Cheng et al. |
| 2015/0139849 A1 | 5/2015 | Pialot, Jr. et al. |
| 2015/0151490 A1 | 6/2015 | Jonasson et al. |
| 2015/0165524 A1 | 6/2015 | Ljungblad et al. |
| 2015/0165525 A1 | 6/2015 | Jonasson |
| 2015/0174658 A1 | 6/2015 | Ljungblad |
| 2015/0174695 A1 | 6/2015 | Elfstroem et al. |
| 2015/0251249 A1 | 9/2015 | Fager |
| 2015/0273622 A1 | 10/2015 | Manabe |
| 2015/0283610 A1 | 10/2015 | Ljungblad et al. |
| 2015/0283613 A1 | 10/2015 | Backlund et al. |
| 2015/0290710 A1 | 10/2015 | Ackelid |
| 2015/0306819 A1 | 10/2015 | Ljungblad |
| 2016/0052056 A1 | 2/2016 | Fager |
| 2016/0052079 A1 | 2/2016 | Ackelid |
| 2016/0054115 A1 | 2/2016 | Snis |
| 2016/0054121 A1 | 2/2016 | Snis |
| 2016/0054347 A1 | 2/2016 | Snis |
| 2016/0059314 A1 | 3/2016 | Ljungblad et al. |
| 2016/0129501 A1 | 5/2016 | Loewgren et al. |
| 2016/0167160 A1 | 6/2016 | Hellestam |
| 2016/0167303 A1 | 6/2016 | Petelet |
| 2016/0202042 A1 | 7/2016 | Snis |
| 2016/0202043 A1 | 7/2016 | Snis |
| 2016/0211116 A1 | 7/2016 | Lock |
| 2016/0279735 A1 | 9/2016 | Hellestam |
| 2016/0282848 A1 | 9/2016 | Hellestam |
| 2016/0303687 A1 | 10/2016 | Ljungblad |
| 2016/0307731 A1 | 10/2016 | Lock |
| 2016/0311021 A1 | 10/2016 | Elfstroem et al. |
| 2017/0080494 A1 | 3/2017 | Ackelid |
| 2017/0087661 A1 | 3/2017 | Backlund et al. |
| 2017/0106443 A1 | 4/2017 | Karlsson |

(56) References Cited

U.S. PATENT DOCUMENTS

| | | |
|---|---|---|
| 2017/0106570 A1 | 4/2017 | Karlsson |
| 2017/0136541 A1 | 5/2017 | Fager |
| 2017/0136542 A1 | 5/2017 | Nordkvist et al. |
| 2017/0173691 A1 | 6/2017 | Jonasson |
| 2017/0189964 A1 | 7/2017 | Backlund et al. |
| 2017/0227417 A1 | 8/2017 | Snis |
| 2017/0227418 A1 | 8/2017 | Snis |
| 2017/0246684 A1 | 8/2017 | Hellestam |
| 2017/0246685 A1 | 8/2017 | Hellestam |
| 2017/0259338 A1 | 9/2017 | Ackelid |
| 2017/0282248 A1 | 10/2017 | Ljungblad et al. |
| 2017/0294288 A1 | 10/2017 | Lock |
| 2017/0341141 A1 | 11/2017 | Ackelid |
| 2017/0341142 A1 | 11/2017 | Ackelid |
| 2017/0348791 A1 | 12/2017 | Ekberg |
| 2017/0348792 A1 | 12/2017 | Fager |
| 2018/0009033 A1 | 1/2018 | Fager |
| 2018/0154444 A1 | 6/2018 | Jonasson |

FOREIGN PATENT DOCUMENTS

| | | |
|---|---|---|
| CN | 101635210 A | 1/2010 |
| CN | 201693176 U | 1/2011 |
| CN | 101607311 B | 9/2011 |
| CN | 203509463 U | 4/2014 |
| DE | 19952998 A1 | 5/2001 |
| DE | 20305843 U1 | 7/2003 |
| DE | 10235434 A1 | 2/2004 |
| DE | 102005014483 A1 | 10/2006 |
| DE | 202008005417 U1 | 8/2008 |
| DE | 102007018601 A1 | 10/2008 |
| DE | 102007029052 A1 | 1/2009 |
| DE | 102008012064 A1 | 9/2009 |
| DE | 102010041284 A1 | 3/2012 |
| DE | 102011105045 B3 | 6/2012 |
| DE | 102013210242 A1 | 12/2014 |
| EP | 0289116 A1 | 11/1988 |
| EP | 0322257 A2 | 6/1989 |
| EP | 0688262 A1 | 12/1995 |
| EP | 1358994 A1 | 11/2003 |
| EP | 1418013 A1 | 5/2004 |
| EP | 1466718 A2 | 10/2004 |
| EP | 1486318 A2 | 12/2004 |
| EP | 1669143 A1 | 6/2006 |
| EP | 1683593 A2 | 7/2006 |
| EP | 1721725 A1 | 11/2006 |
| EP | 1752240 A1 | 2/2007 |
| EP | 1952932 A2 | 8/2008 |
| EP | 2011631 A1 | 1/2009 |
| EP | 2119530 A1 | 11/2009 |
| EP | 2281677 A1 | 2/2011 |
| EP | 2289652 A1 | 3/2011 |
| EP | 2292357 A1 | 3/2011 |
| EP | 2832474 A1 | 2/2015 |
| FR | 2980380 A1 | 3/2013 |
| JP | H05-171423 A | 7/1993 |
| JP | 2003241394 A | 8/2003 |
| JP | 2003245981 | 9/2003 |
| JP | 2009006509 A | 1/2009 |
| SE | 524467 C2 | 8/2004 |
| WO | WO 1993/008928 | 5/1993 |
| WO | WO 1996/012607 A1 | 5/1996 |
| WO | WO 1997/037523 A2 | 10/1997 |
| WO | WO 2001/081031 A1 | 11/2001 |
| WO | WO 2001/085386 A2 | 11/2001 |
| WO | WO 2002/008653 A1 | 1/2002 |
| WO | WO 2004/007124 A1 | 1/2004 |
| WO | WO 2004/043680 A2 | 5/2004 |
| WO | WO 2004/054743 A1 | 7/2004 |
| WO | WO 2004/056511 A1 | 7/2004 |
| WO | WO 2004/106041 A2 | 12/2004 |
| WO | WO 2004/108398 A1 | 12/2004 |
| WO | WO 2006/091097 A2 | 8/2006 |
| WO | WO 2006/121374 A1 | 11/2006 |
| WO | WO 2007/112808 A1 | 10/2007 |
| WO | WO 2007/147221 A1 | 12/2007 |
| WO | WO 2008/013483 A1 | 1/2008 |
| WO | WO 2008/057844 A1 | 5/2008 |
| WO | WO 2008/074287 A1 | 6/2008 |
| WO | WO 2008/125497 A1 | 10/2008 |
| WO | WO 2008/147306 A1 | 12/2008 |
| WO | WO 2009/000360 A1 | 12/2008 |
| WO | WO 2009/072935 A1 | 6/2009 |
| WO | WO 2009/084991 A1 | 7/2009 |
| WO | WO 2010/095987 A1 | 8/2010 |
| WO | WO 2010/125371 A1 | 11/2010 |
| WO | WO 2011/008143 A1 | 1/2011 |
| WO | WO 2011/011818 A1 | 2/2011 |
| WO | WO 2011/030017 A1 | 3/2011 |
| WO | WO 2011/060312 A2 | 5/2011 |
| WO | WO 2012/102655 A1 | 8/2012 |
| WO | WO 2013/092997 A1 | 6/2013 |
| WO | WO 2013/098050 A1 | 7/2013 |
| WO | WO 2013/098135 A1 | 7/2013 |
| WO | WO 2013/159811 A1 | 10/2013 |
| WO | WO 2013/167194 A1 | 11/2013 |
| WO | WO 2013/178825 A2 | 12/2013 |
| WO | WO 2014/071968 A1 | 5/2014 |
| WO | WO 2014/092651 A1 | 6/2014 |
| WO | WO 2014/095200 A1 | 6/2014 |
| WO | WO 2014/095208 A1 | 6/2014 |
| WO | WO 2014/195068 A1 | 12/2014 |
| WO | WO 2015/032590 A2 | 3/2015 |
| WO | WO 2015/091813 A1 | 6/2015 |
| WO | WO 2015/120168 A1 | 8/2015 |
| WO | WO 2015/142492 A1 | 9/2015 |

OTHER PUBLICATIONS

Arcam AB, Applicant's Reply to ISA's Mar. 8, 2013 Written Opinion for International Application No. PCT/EP2012/074535, dated Sep. 5, 2013, 3 pages.

International Searching Authority (ISA), Second Written Opinion for International Application No. PCT/EP2012/074535, dated Dec. 12, 2013, 5 pages, European Patent Office, The Netherlands.

International Preliminary Examining Authority, International Preliminary Report on Patentability for International Application No. PCT/EP2012/074535, including Applicant's Feb. 10, 2014 Reply to the Second Written Opinion dated Dec. 12, 2013, dated Mar. 12, 2014, 18 pages, European Patent Office, The Netherlands.

Cheah, Chi-Mun, et al., "Automatic Algorithm for Generating Complex Polyhedral Scaffold Structure for Tissue Engineering", Tissue Engineering, 2004, pp. 595-610, vol. 10, No. 3/4, XP002691483.

Guibas, Leonidas J., et al., "Randomized Incremental Construction of Delaunay and Voronoi Diagrams", Algorithmica, Jun. 1992, pp. 381-413, vol. 7, Issue 1-6, Springer-Verlag, New York.

Weigel, T., et al., "Design and Preparation of Polymeric Scaffolds for Tissue Engineering," Expert Rev. Med. Devices, 2006, pp. 835-851, vol. 3, No. 6, XP002691485.

Yang, et al., "The Design of Scaffolds for Use in Tissue Engineering, Part II, Rapid Prototyping Techniques", Tissue Engineering, 2002, pp. 1-11, vol. 8, No. 1, XP002691484.

Gibson, D.W., et al., "Additive Manufacturing Technologies: Rapid Prototyping to Direct Digital Manufacturing", 2010, pp. 126-129, Springer, New York.

Motojima, Seiji, et al., "Chemical Vapor Growth of LaB6 Whiskers and Crystals Having a Sharp Tip", Journal of Crystal Growth, vol. 44, No. 1, Aug. 1, 1978 (Aug. 1, 1978), pp. 106-109.

Klassen, Alexander, et al., "Modelling of Electron Beam Absorption in Complex Geometries", *Journal of Physics D: Applied Physics*, Jan. 15, 2014, 12 pages, vol. 47, No. 6, Institute of Physics Publishing Ltd., Great Britain.

METHOD AND APPARATUS FOR DETECTING DEFECTS IN FREEFORM FABRICATION

CROSS REFERENCE TO RELATED APPLICATIONS

This application is a national stage application, filed under 35 U.S.C. § 371, of International Application No. PCT/EP2012/074535, filed Dec. 5, 2012, which claims priority to U.S. Provisional Application No. 61/580,766, filed Dec. 28, 2011, the contents of both which are hereby incorporated by reference in their entirety.

BACKGROUND

Related Field

The present invention relates to a method and an apparatus for detecting defects according to the claims recited herein.

Description of Related Art

Freeform fabrication or additive manufacturing is a method for forming three-dimensional articles through successive fusion of chosen parts of powder layers applied to a worktable. A method and apparatus according to this technique is disclosed in US 2009/0152771.

Such an apparatus may comprise a work table on which said three-dimensional article is to be formed, a powder dispenser, arranged to lay down a thin layer of powder on the work table for the formation of a powder bed, a ray gun for delivering energy to the powder whereby fusion of the powder takes place, elements for control of the ray given off by the ray gun over said powder bed for the formation of a cross section of said three-dimensional article through fusion of parts of said powder bed, and a controlling computer, in which information is stored concerning consecutive cross sections of the three-dimensional article. A three-dimensional article is formed through consecutive fusions of consecutively formed cross sections of powder layers, successively laid down by the powder dispenser.

In US 2009/0152771 it is provided a camera for capturing an Infrared-radiation image, more particularly this camera is used for detecting irregularities in a newly applied powder layer. The irregularities may, according to US 2009/0152771, be caused by irregular applying of the powder on the working table or contamination in the powder dispenser or impurities in the powder as such. A problem with this defect detection method is that not all of the irregularities that are detected will cause a real defect in the three-dimensional article, i.e., false defects may be detected causing unnecessary actions and/or rejections of the article to be produced.

BRIEF SUMMARY

An object of the invention is to provide a method and apparatus for increasing the reliability of the defect detection and thereby decreasing the amount of false defect detection and unnecessary rejection of a three-dimensional articles produced by freeform fabrication or additive manufacturing.

The abovementioned object is achieved by the features in the method and apparatus claims recited herein.

In a first aspect of the invention it is provided a method for detecting defects when forming a three-dimensional article through successive fusion of parts of a powder bed, which parts corresponds to successive cross sections of the three-dimensional article. Said method comprising the steps of:

a. providing a model of said three dimensional article,
b. providing a first powder layer on a work table,
c. directing an energy beam over said work table causing said first powder layer to fuse in selected locations according to said model to form a first cross section of said three-dimensional article,
d. providing a second powder layer on said work table,
e. directing the energy beam over said work table causing said second powder layer to fuse in selected locations according to said model to form a second cross section of said three-dimensional article, wherein said second layer is bonded to said first layer,
f. capturing at least one first image of at least a first fusion zone of said first powder layer,
g. capturing at least one second image of at least a second fusion zone of said second powder layer, wherein said second fusion zone is at least partly overlapping said first fusion zone,
h. comparing said first and second images with corresponding layers in said model,
i. detecting a defect in the three-dimensional article if a deviation in said first image with respect to said model is at least partially overlapping a deviation in said second image with respect to said model.

By providing a comparison of at least two consecutive layers of melted powder with corresponding layers of the model, the likelihood of false defect detection is greatly reduced. Since it is two consecutive layers of a melted structure of a true article which is compared with corresponding layers of said model rather than looking at a powder layer before fusing together the particles in said powder layer, a more reliable conclusion of a true defect in the final article can be performed.

In one example embodiment of the present invention a deviation of the first image in the first layer relative to a corresponding layer in said model is completely overlapping with a deviation in a second image of an adjacent layer relative to a corresponding layer in said model.

In still another example embodiment of the present invention the corresponding layers in said model may be a reference image. Said reference image may be a simulated image or an image of a previous layer without defects.

The advantage of having simulated images to compare with the actual images of the fusion zone is that they are easy and quick to generate compared to if the reference images are actual images taken from a previous build process of a three dimensional article. An advantage of comparing the actual captured image to a corresponding actual layer of the CAD model is that it is efficient, fast and reliable.

In another example embodiment said detected defect is repaired by remelting the defect and a predetermined area surrounding said defect.

An advantage of this example embodiment is that the defect is not only detected but also repaired.

In yet another example embodiment said detected defect is repaired by increasing the power and/or the time said energy beam is present when fusing the powder layer above and a predetermined distance around said defect.

An advantage of this embodiment is that it takes a minimum amount of time to repair the defect since it only involves a change in the power of the energy beam for a short period of time and/or increasing the time the beam is present at and around the defect when melting the powder layer.

In another aspect of the present invention it is provided an apparatus for detecting defects when forming a three-dimensional article through successive fusion of parts of a powder bed, which parts corresponds to successive cross sections of the three-dimensional article, said method comprising the steps of:
a. means for providing a model of said three dimensional article,
b. means for providing a first powder layer on a work table,
c. means for directing an energy beam over said work table causing said first powder layer to fuse in selected locations according to said model to form a first cross section of said three-dimensional article,
d. means for providing a second powder layer on said work table,
e. means for directing the energy beam over said work table causing said second powder layer to fuse in selected locations according to said model to form a second cross section of said three-dimensional article, wherein said second layer is bonded to said first layer,
f. means for capturing at least one first image of at least a first fusion zone of said first powder layer,
g. means for capturing at least one second image of at least a second fusion zone of said second powder layer, wherein said second fusion zone is at least partly overlapping said first fusion zone,
h. means for comparing said first and second image with corresponding layers in said model,
i. means for detecting a defect in the three-dimensional article if a deviation in said first image with respect to said model is at least partially overlapping a deviation in said second image with respect to said model.

With such an apparatus articles may be produced which can be controlled during manufacturing if there is one or more defects present.

BRIEF DESCRIPTION OF THE FIGURES

The invention will be further described in the following, in a non-limiting way with reference to the accompanying drawings. Same characters of reference are employed to indicate corresponding similar parts throughout the several figures of the drawings.

DETAILED DESCRIPTION OF VARIOUS EMBODIMENTS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "three-dimensional structures" and the like as used herein refer generally to intended or actually fabricated three-dimensional configurations (e.g. of structural material or materials) that are intended to be used for a particular purpose. Such structures, etc. may, for example, be designed with the aid of a three-dimensional CAD system.

The term "electron beam" as used herein in various embodiments refers to any charged particle beam. The source of a charged particle beam can include an electron gun, a linear accelerator and so on.

Figure 3:
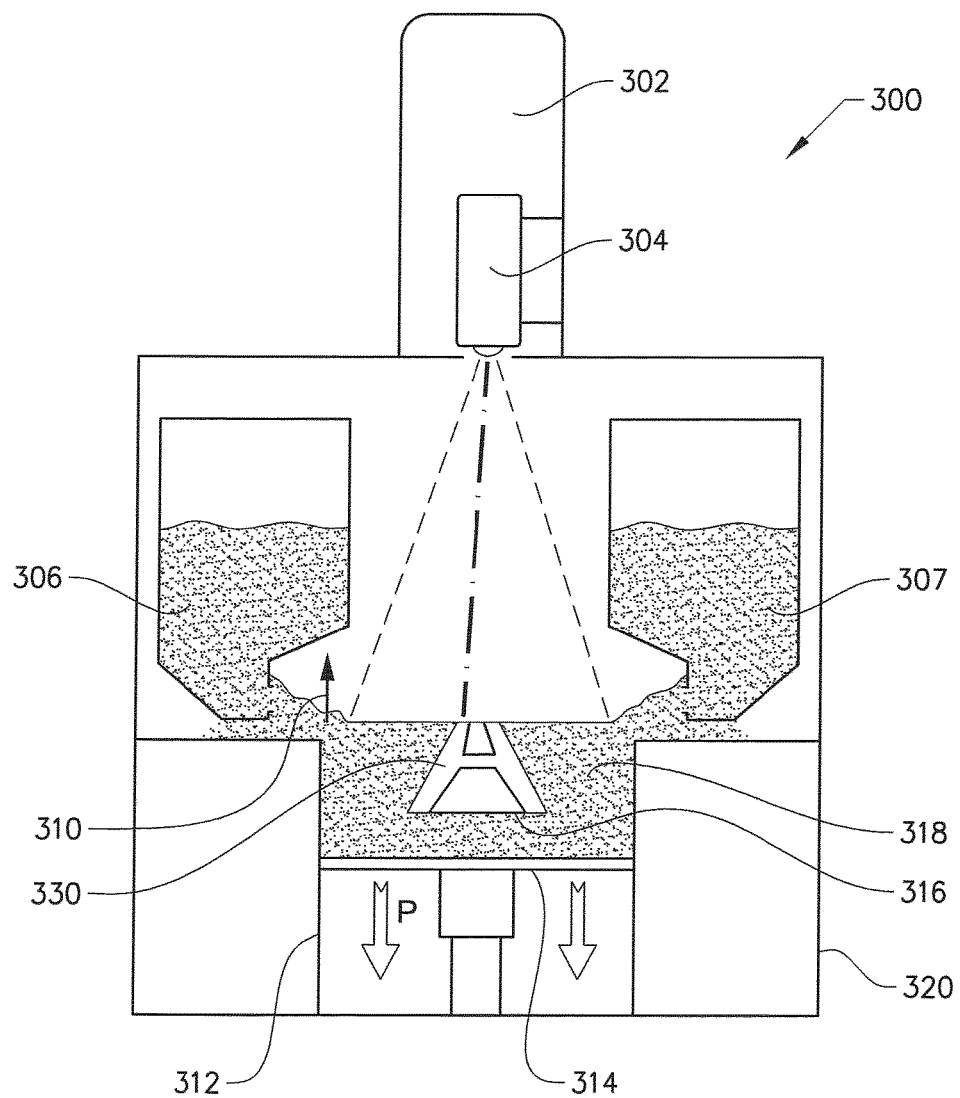
FIG. 3 depicts an apparatus according to an embodiment of the present invention.

FIG. 3 depicts an embodiment of a freeform fabrication or additive manufacturing apparatus 300 according to of the present invention. Said apparatus 300 comprising an electron gun 302; a camera 304; two powder hoppers 306, 307; a start plate 316; a build tank 312; a powder distributor 310; a build platform 314; and a vacuum chamber 320.

The vacuum chamber 320 is capable of maintaining a vacuum environment by means of a vacuum system, which system may comprise a turbomolecular pump, a scroll pump, an ion pump and one or more valves which are well known to a skilled person in the art and therefore need no further explanation in this context. The vacuum system is controlled by a control unit.

The electron gun 302 is generating an electron beam which is used for melting or fusing together powder material 318 provided on the start plate 316. At least a portion of the electron gun 302 may be provided in the vacuum chamber 320. A control unit may be used for controlling and managing the electron beam emitted from the electron beam gun 302. At least one focusing coil (not shown), at least one deflection coil and an electron beam power supply may be electrically connected to said control unit. In an example embodiment of the invention said electron gun generates a focusable electron beam with an accelerating voltage of about 60 kV and with a beam power in the range of 0-3 kW. The pressure in the vaccum chamber may be in the range of $10^{-3}$-$10^{-6}$ mBar when building the three-dimensional article by fusing the powder layer by layer with the energy beam.

Instead of melting the powder material with an electron beam a laser beam may be used.

The powder hoppers 306, 307 comprise the powder material to be provided on the start plate 316 in the build tank 312. The powder material may for instance be pure metals or metal alloys such as titanium, titanium alloys, aluminum, aluminum alloys, stainless steel, Co—Cr—W alloy, etc.

The powder distributor 310 is arranged to lay down a thin layer of the powder material on the start plate 316. During a work cycle the build platform 314 will be lowered successively in relation to the ray gun after each added layer of powder material. In order to make this movement possible, the build platform 314 is in one embodiment of the invention arranged movably in vertical direction, i.e., in the direction indicated by arrow P. This means that the build platform 314 starts in an initial position, in which a first powder material layer of necessary thickness has been laid down on said start plate 316. A first layer of powder material may be thicker than the other applied layers. The reason for starting with a first layer which is thicker than the other layers is that one does not want a melt-through of the first layer onto the start plate. The build platform is thereafter lowered in connection with laying down a new powder material layer for the formation of a new cross section of a three-dimensional article. Means for lowering the build platform 314 may for instance be through a servo engine equipped with a gear, adjusting screws etc.

In an example embodiment of a method according to the present invention for detecting defects when forming a three-dimensional article through successive fusion of parts of a powder bed, which parts corresponds to successive cross sections of the three-dimensional article, comprising a first step 402 of providing a model of said three dimensional article. Said model may be generated via a CAD (Computer Aided Design) tool.

In a second step 404 a first powder layer is provided on the work table 316. Powder may be distributed evenly over the worktable according to several methods. One way to distribute the powder is to collect material fallen down from the hopper 306, 307 by a rake system. The rake is moved over the build tank thereby distributing the powder over the start plate. The distance between a lower part of the rake and the upper part of the start plate or previous powder layer determines the thickness of powder distributed over the start plate. The powder layer thickness can easily be adjusted by adjusting the height of the build platform 314.

In a third step 406 an energy beam is directed over said work table 316 causing said first powder layer to fuse in selected locations to form a first cross section of said three-dimensional article. The energy beam may be an electron beam or a laser beam. The beam is directed over said work table 316 from instructions given by a control unit (not shown). In the control unit instructions for how to control the beam gun for each layer of the three-dimensional article is stored.

Figure 4:
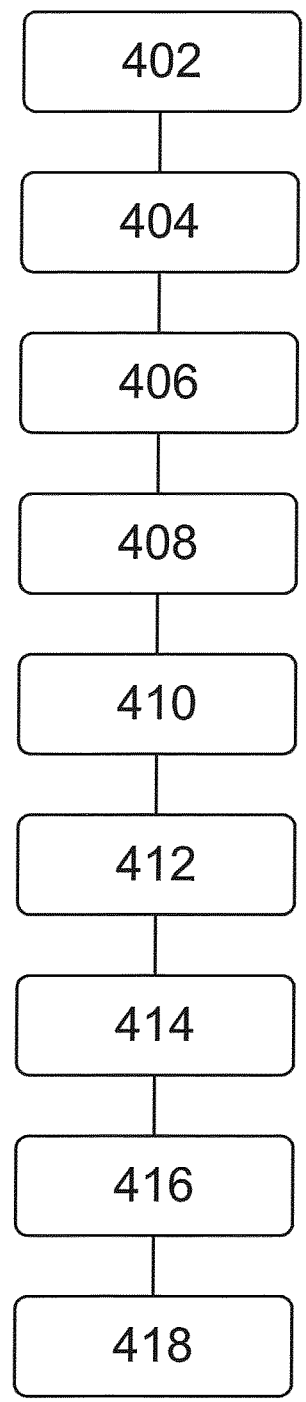
FIG. 4 depicts a flow chart of the method according to an embodiment of the present invention.

After a first layer is finished, i.e., the fusion of powder material for making a first layer of the three-dimensional article, a second powder layer is provided on said work table 316 denoted by step 408 in FIG. 4. The second powder layer is preferably distributed according to the same manner as the previous layer. However, there might be alternative methods in the same additive manufacturing machine for distributing powder onto the work table. For instance, a first layer may be provided by means of a first powder distributor, a second layer may be provided by another powder distributor. The design of the powder distributor is automatically changed according to instructions from the control unit. A powder distributor in the form of a single rake system, i.e., where one rake is catching powder fallen down from both a left powder hopper 306 and a right powder hopper 307, the rake as such can change design.

After having distributed the second powder layer on the work table 316, the energy beam is directed over said work table causing said second powder layer to fuse in selected locations to form a second cross section of said three-dimensional article denoted by step 410 in FIG. 4. Fused portions in the second layer may be bonded to fused portions of said first layer. The fused portions in the first and second layer may be melted together by melting not only the powder in the uppermost layer but also remelting at least a fraction of a thickness of a layer directly below said uppermost layer.

After having fused selected portions of said first powder layer, at least one first image is captured of at least a first fusion zone of said first powder layer denoted by step 412 in FIG. 4. The image is taken by the camera 304 provided inside or outside the vacuum chamber 320. The camera 304 may be any type of camera for example an IR-camera (Infrared-camera), NIR-camera (Near Infrared-camera), a VISNIR-camera (Visual Near Infrared-camera), a CCD camera (Charged Coupled Device-camera), a CMOS-camera (Complementary Metal Oxide Semiconductor-camera), a digital camera.

Figure 1A:
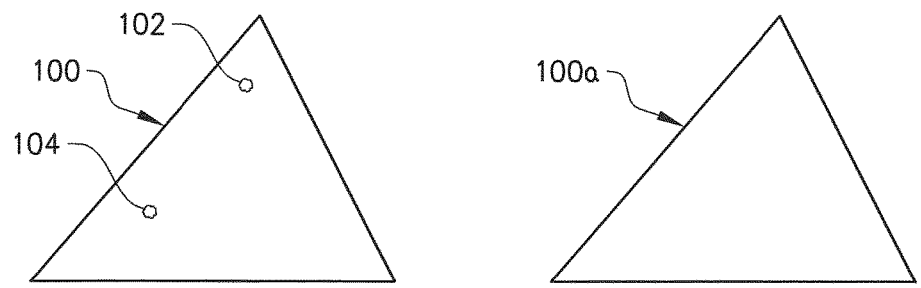
FIG. 1a depicts a top view image (left) of a first fused powder layer and a corresponding first reference image (right) of the first fused powder layer.

In FIG. 1a two images 100, 100a are depicted, where the left image 100 illustrates an image of an arbitrary layer, for instance the first layer, of a three-dimensional article and the right image 100a is a reference image of the same layer of the three-dimensional article as in the left image 100. The reference image may be a layer from the model in a CAD file representing the 3-dimensional article to be manufactured. The reference image may be a picture taken from a defect free area. The reference image may be an image from a previous layer if said layer is defect free. The reference image may also be a simulation of the fused powder layer. The left image 100 is an image of at least a portion of the fusion zone of said first layer of said three-dimensional article. In said image there are two defects 102, 104 in the fusion zone. The defects may be caused by irregular powder distribution, irregular size of the powder material, cavities inside the powder material, different alloy structure of said powder material, a power peak of the radiation gun which is fusing the powder material and/or a local deviation in a scan speed of the radiation gun. If the scan speed is suddenly interrupted for a short time, too much power from the radiation gun will be delivered to a specific area of said first powder material layer, which may cause the material not only to melt but to boil which in turn may cause defects in the fused layer. The image in the form of the triangle to the left in FIG. 1a may be a portion of a fusion zone of one layer of the three-dimensional article. Said portion of the fusion zone may be selected depending on the resolution of the sensitive camera. With a camera having higher resolution a smaller fusion zone can be chosen, and thereby capable of detecting smaller defects, compared to a camera with lower resolution. The fusion zone in FIG. 1a is illustrated to be triangular, which is just an example. Of course the shape of the chosen fusion zone may be of any particular form depending inter alia on where said fusion zone is selected from the over-all fusion zone of the first layer and/or the shape of the fusion zone selected by the operator of the camera. The camera may be a heat sensitive camera and the first and second images may be heat images taken by said heat sensitive camera.

The first image of the first fusion zone of the first powder layer may be compared with the first reference image of the first fusion zone of the first powder layer. In an alternative embodiment the first image of the first fusion zone of the first powder layer may be compared with a corresponding layer in said model. As can be seen from FIG. 1a, the first image 100 of the first fusion zone of the first powder layer is different to the first reference image of the first fusion zone of the first powder layer. The difference is the two defects 102 and 104. The defects may be in the form of cavities or irregularities in the fused layer which are large enough for the camera to capture a deviation. The comparison of the image to the reference image is performed by using ordinary image recognising software. The comparison of real images with reference images is denoted by 414 in FIG. 4.

The energy beam, which may be a laser beam or an electron beam, not only melts the last applied powder layer but also at least the layer of material below the powder layer resulting in a melt comprising the powder material and already melted material from a previous fusion process. A defect may only be detected if a deviation from the captured image of a fusion zone to a model is detected in two consecutive layers and where the deviations are at least partially overlapping each other.

Figure 1B:
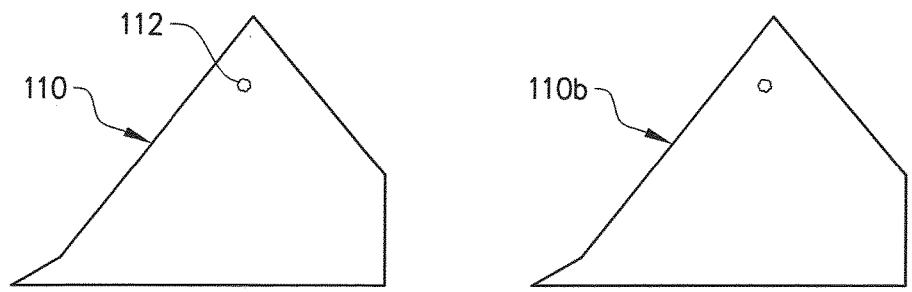
FIG. 1b depicts a top view image (left) of a second fused powder layer and a corresponding second reference image (right) of the second fused powder layer.

At least one second image is captured of at least a second fusion zone of said second powder layer denoted by 414 in FIG. 4. The second image is taken by the camera 304 provided in the vacuum chamber 320. In FIG. 1b two images 110, 110b are depicted, where the left image 110 illustrates an image of the second layer, of a three-dimensional article and the right image 110b is a reference image of the same layer of the three-dimensional article as in the left image 110. The left image 110 is an image of at least a portion of the fusion zone of said second layer of said three-dimensional article. In said image there is one defect 112 in the fusion zone.

The second image 110 of the second fusion zone of the second powder layer is compared with the second reference image of the second fusion zone of the second powder layer. The comparison of the first image 100 and the second image 110 with corresponding layers in said model is denoted by 416 in FIG. 4. As can be seen from FIG. 1b, the second image 110 of the second fusion zone of the second powder layer is different to the second reference image of the second fusion zone of the second powder layer. The difference is the defect 112. The defect may be in the form of cavities or irregularities in the fused layer which are large enough for the camera to capture a deviation.

The second fusion zone is at least partly overlapping said first fusion zone.

Figure 2:
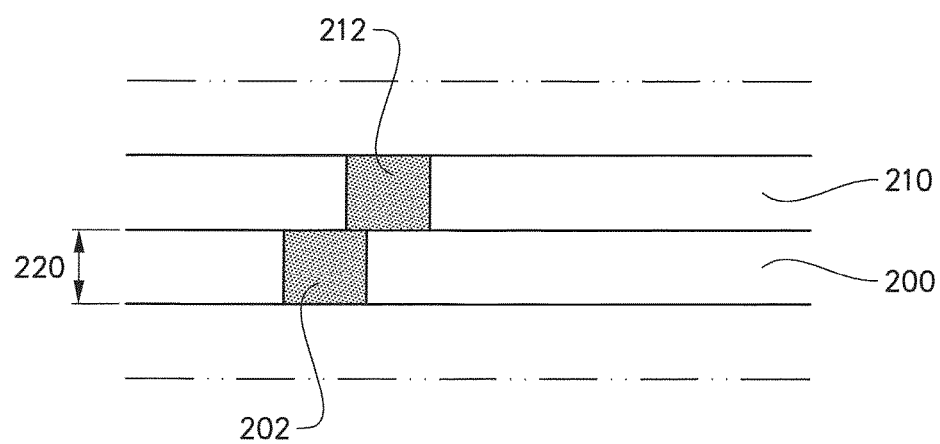
FIG. 2 depicts a side view image of a first and a second fused powder layer.

A defect in the three-dimensional article is detected if a deviation in said first image with respect to said first reference image is at least partially overlapping a deviation in said second image with respect to said second reference image denoted by step 418 in FIG. 4. FIG. 2 is a partial side view illustrating two layers of a three-dimensional article made by fusing layers together according to the method as disclosed above. A first layer is denoted 200 and a second layer is denoted 210. Of course there might be one or several layers below and above the illustrated first 200 and second 210 layers. The first layer 200 comprises a first defect 202 and the second layer 210 comprises a second defect 212.

Said first and second defects are partially overlapping each other, i.e., the second defect 212 in the second layer 210 is partially overlapping the first defect 202 in the first layer 200. The first layer 200 in FIG. 2 may represent the left image in FIG. 1a and the second layer 210 may represent the left image in FIG. 1b. The first defect 202 in the first layer in FIG. 2 may represent defect 102 in the left image of FIG. 1a. The second defect 212 in the second layer of FIG. 2 may represent the defect 112 in the left image of FIG. 1b. The thickness of a layer is denoted 220 in FIG. 2. The thickness of a powder layer may be in the range of 30-150 μm. The size of the metal particles in the powder material may be in the range of 45-150 μm. The powder material may also be in the range of 25-45 μm.

Defects in the three-dimensional article which are below 100 μm in size may be healed by Hot Isostatic Pressure (HIP).

Said reference image may be constructed by means of a simulation of the fusion of a given powder layer for forming one layer of a three-dimensional structure. In an example embodiment one is using a unique reference image for each layer of the three-dimensional article to be produced. This means that an image of layer n of the three-dimensional article is correlated with a reference image n and an image of layer n+1 of the three-dimensional article is correlated with a reference image n+1, where n is an integer going from 1 to the number of layers of the article to be produced. In an alternative example embodiment one is using the same reference image for layers having equal shape, i.e., if two consecutive layers are equal one can of course use the same reference image. If two layers only differ to each other in the outer contour, one may have a single reference image covering the outer shape of the two layers.

A detected defect may be repaired during the manufacturing process. The repair process may for instance comprise a method of remelting the detected defect area and a predetermined area surrounding said defect without applying a new powder layer. By doing so the appearance of the defect may be smoothened out and may be healed in a next fusion process. This is because the new powder material which is applied on top of the more evenly distributed defect is more likely to have a thickness which will not create another defect when fused. If applying a powder layer on a non modified defect, the powder may at this defect position have a thickness which is larger than the melting capability of the energy beam. This in turn may cause a hollow structure comprising unfused powder material in the finished article.

An alternative repairing method may be to apply a new powder material layer. Since the position of the defect is known the energy beam may increase its power at the defect position in order to melt all powder material and/or increase the time said energy beam is present at and around the defect position. This process may be repeated for one or several powder layers in order to repair the defect.

In an alternative method one may combine the method of smoothen out the detected defect by refusing the defect and a predetermined area around the defect without applying new material with the method of increasing the power of the energy beam and/or the time said energy beam is present at and a predetermined distance around the defect area when melting the powder layer. The predetermined distance around said defect may be in the range of 0-few mm from the centre of the defect.

In another example embodiment the powder layer comprising fused and non-fused powder may be illuminated by a illumination source. The illumination source may be ordinary white light or any light within a predetermined wavelength range, for instance blue light, red light, or green light.

In an example embodiment the camera which is capturing images of the powder layer may be provided with a appropriate filter. If the illumination source is radiation blue light onto the powder layer, said camera may be provided with a band pass filter allowing only blue light to be detected by the camera.

In another example embodiment said camera may be provided with a long pass filter allowing only IR radiation to be detected by the camera. In an example embodiment it is provided a mechanism for switching between said band pass filter and said long pass filer. The band pass filter may be used when the powder layer is illuminated with a wavelength falling within the band of said band pass filter. A long pass filer may be used when no illumination source is used for illuminating the powder layer, i.e., pure self radiation (IR) from the powder layer.

In an example embodiment at least one first image may be taken from powder layer N without using an illumination source and with said long pass filter in-front of the camera. At least one second image may be taken from powder layer N when using an illumination source and with said band pass filter in-front of the camera. The illumination source is having a wavelength within the wavelength range of the band pass filter. Said first and second images may be correlated in order to enhance the information from a specific powder layer.

The image taken by the camera may be treated in a imaging program. Pixels in the image may for instance have local threshold levels depending on the pixels specific position and its surrounding. White or black, which may mean fused or non fused positions, may have different threshold levels depending on the position of the pixel in the camera image.

A plurality of images may be taken from one and the same powder layer and be used in an imaging program for removing noise.

In an example embodiment of the invention the power of the energy beam may be increased or decreased when remelting a predetermined position which may comprise a defect. The time the energy beam is present at a specific location, which may be a detected defect, may be increased or decreased when remelting the defect position.

The invention is not limited to the above-described embodiments and many modifications are possible within the scope of the following claims. Such modifications may, for example, involve using a different source of ray gun than the exemplified electron beam such as laser beam. Other materials than metallic powder may be used, such as powder of polymers and powder of ceramics. Images taken from more than 2 layers may also be possible, i.e., in an alternative embodiment of the present invention for detecting a defect at least one image from at least three, four or more layers are used. A defect may be detected if the defect position in said three, four or more layers are at least partly overlapping each other. The thinner the powder layer the more powder layers may be used in order to detect a factual defect.

The invention claimed is:

1. A method for detecting defects when forming a three-dimensional article through successive fusion of parts of a powder bed, which parts corresponds to successive cross sections of the three-dimensional article, said method comprising the steps of:
   providing a model of said three dimensional article;
   providing a first powder layer on a work table;
   directing an energy beam over said work table causing said first powder layer to fuse in selected locations according to said model to form a first cross section of said three-dimensional article;
   providing a second powder layer on said work table;
   directing the energy beam over said work table causing said second powder layer to fuse in selected locations according to said model to form a second cross section of said three-dimensional article, wherein said second layer is bonded to said first layer;
   capturing at least one first heat image of at least a first fusion zone of said first powder layer after having fused selected portions of said first powder layer;
   capturing at least one second heat image of at least a second fusion zone of said second powder layer after having fused selected portions of said second powder layer, wherein said second fusion zone is at least partly overlapping said first fusion zone;
   comparing said first and second heat images with corresponding layers in said model;
   determining a first deviation in said first image with respect to said model, wherein the first deviation comprises at least one of cavities or irregularities in the first fused layer that are large enough for the camera to capture;
   determining a second deviation in said second image with respect to said model, wherein the second deviation comprises at least one of cavities or irregularities in the second fused layer that are large enough for the camera to capture;
   responsive only to detecting at least a partial overlap of said first deviation and said second deviation, identifying a defect in the three-dimensional article; and
   repairing the identified defect by either:
      re-melting the defect and a predetermined area surrounding said defect to smooth out the defect surface and healing the defect in a process of fusing a third powder layer, wherein the re-melting of the defect and the predetermined area surrounding said defect in the process of fusing the third powder layer is by at least one of increasing the power of the energy beam or increasing the time said energy beam is present at the defect position and the predetermined area surrounding said defect, or
      re-fusing the identified defect and a predetermined area around said defect via at least one of increasing or decreasing the power of the energy beam or decreasing or increasing the time said energy beam is present.

2. The method according to claim 1, wherein said model, to which said images are compared to, is a CAD-model.

3. The method according to claim 1, wherein said energy beam is an electron beam.

4. The method according to claim 1, wherein said powder is metallic powder.

5. The method according to claim 1, wherein said image is captured by an IR-camera.

6. The method according to claim 1, wherein said model comprises simulated reference images corresponding to building layers of said three-dimensional article.

* * * * *